United States Patent [19]

Chupp

[11] 4,261,733
[45] Apr. 14, 1981

[54] HERBICIDAL COMPOUNDS AND METHOD OF PREPARATION AND USE

[75] Inventor: John P. Chupp, Kirkwood, Mo.

[73] Assignee: Monsanto Company, St. Louis, Mo.

[21] Appl. No.: 965,353

[22] Filed: Nov. 30, 1978

[51] Int. Cl.³ ................. A01N 37/18; C07C 103/12
[52] U.S. Cl. ............................... 71/118; 71/88; 260/340.7; 260/338; 564/214
[58] Field of Search ................. 71/118; 260/562 B

[56] References Cited

U.S. PATENT DOCUMENTS

| | | | |
|---|---|---|---|
| 3,257,190 | 6/1966 | Soper | 71/118 |
| 3,551,132 | 12/1970 | Husted | 71/118 |
| 3,966,811 | 6/1976 | Krenzer | 71/118 |
| 3,976,471 | 8/1976 | Richter et al. | 71/118 |
| 4,019,894 | 4/1977 | Vogel et al. | 71/118 |

FOREIGN PATENT DOCUMENTS

| | | | |
|---|---|---|---|
| 2402983 | 8/1974 | Fed. Rep. of Germany | 71/118 |
| 2215170 | 9/1974 | France | 71/118 |

Primary Examiner—Glennon H. Hollrah
Attorney, Agent, or Firm—Patricia A. Coburn; Donald W. Peterson

[57] ABSTRACT

The disclosure herein relates to a new class of herbicidal compounds comprising 2'-alkyl-6'-(2,2-dialkoxyethyl)-N-(alkoxymethyl)-2-haloacetanilides, herbicidal compositions containing same, their method of preparation and use to selectively control undesired vegetation in agricultural crops, e.g., monocotyledons such as wheat, sorghum and rice and dicotyledons such as sugarbeets and soybeans.

9 Claims, No Drawings

HERBICIDAL COMPOUNDS AND METHOD OF PREPARATION AND USE

BACKGROUND OF THE INVENTION

The invention herein pertains to the field of herbicidal compositions and method of use thereof. In more particular, the herbicidal compositions herein have particular application in the control of undesired plants associated with monocotyledons such as wheat, sorghum and rice and dicotyledons such as sugarbeets and soybeans.

DESCRIPTION OF THE PRIOR ART

It is known in the prior art to prepare 2-haloacetanilides having a variety of substituents on the phenyl ring and on the anilide nitrogen atom.

As more or less relevant to the compounds of this invention the prior art discloses various 2-haloacetanilides which may be substituted with alkyl and/or alkoxyalkyl radicals on the phenyl ring and other substituents on the nitrogen atom including alkoxyalkyl or dialkoxyalkyl. See, for example, French Pat. No. 2,215,170 and U.S. Pat. Nos. 3,966,811 and 3,976,471.

Said 2,215,170 French patent discloses herbicidal compounds which may be substituted with alkyl and alkoxyalkyl radicals in the 2' and 6' positions and with an alkoxyalkyl radical on the nitrogen atom. However, the alkoxyalkyl radical on the nitrogen atom in said 2,215,170 patent must have no less than two carbon atoms separating the nitrogen and oxygen atoms as distinguished from alkoxymethyl-substituted 2-haloacetanilides. Moreover, the ring-substituted alkoxyalkyl radical in said 2,215,170 French patent does not encompass the dialkoxyalkyl radicals according to the compounds of this invention.

The U.S. Pat. Nos. 3,966,811 and 3,976,471 disclose compounds which may be substituted with alkoxyalkyl radicals on the phenyl ring, but not in either of the ortho (2' and 6') positions as required in the present invention. Moreover, the nitrogen substituents in the 3,966,811 and 3,976,471 patents are distinct from those herein; that in 3,966,811 patent being a 2,2-dialkoxyethyl radical and that in the 3,976,471 patent being an alkylideneaminooxymethyl radical.

Other less relevant prior art compounds include 2-haloacetanilides which may be substituted with alkoxyalkyl or dialkoxyalkyl radicals on the nitrogen atom, but not on the phenyl ring; typical of such compounds are those described in U.S. Pat. Nos. 3,442,945, 3,547,620, 3,983,174, 3,952,056, 3,937,730, 4,019,894, 4,025,554 and 4,086,080.

As relevant to the novel process herein, the closest known prior art (relevant only to separate parts of the overall process described herein) appears to be papers published by P. G. Gassman et al in Tetrahedron Letters, page 497 (1972) and P. G. Gassman et al in J. Amer. Chem. Society, 96, 5487 (1974) and U.S. Pat. No. 3,637,847 and the above-mentioned U.S. Patents 3,442,945 and 3,547,620. The Gassman et al papers describe procedures for preparing certain o-substituted anilines. These methods involve reacting t-butylhypochlorite with a primary or secondary amine to prepare the N-chloro-substituted derivative thereof followed by reaction with an alkyl methyl sulfide to produce the corresponding sulfilimine or sulfonium salt. Rearrangement of said salt and reaction with Raney nickel produces the desired o-substituted aniline. The Gassman et al procedures can be used to produce the intermediate primary amines used as starting materials in the process disclosed and claimed herein.

The above 3,637,847 patent describes the reaction of primary amines with formaldehyde and haloacetylating the reaction product to form the corresponding phenyl-substituted-N-halomethyl-2-haloacetanilide. Said 3,442,945 and 3,547,620 patents describe the reaction of compounds disclosed in said 3,637,847 patent with an alcohol to produce the corresponding 2-haloacetanilide.

SUMMARY OF THE INVENTION

The present invention relates to a new class of herbicidal compounds comprising 2'-alkyl-6'-(2,2-dialkoxyethyl)-N-(alkoxymethyl)-2-haloacetanilides, process for preparing these compounds, herbicidal compositions containing said compounds as active ingredient and herbicidal method of use, particularly to control noxious weeds in soybeans, sugar-beets, wheat, rice and sorghum.

In more particular, the compounds of this invention are those having the formula

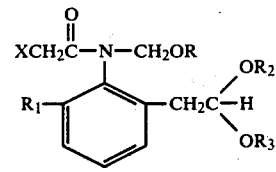

wherein X represents halogen, particularly chlorine, bromine or iodine and R, $R_1$, $R_2$ and $R_3$ represent $C_{1-10}$ alkyl radicals, which may be the same or different, particularly $C_{1-5}$ lower alkyls. $R_2$ and $R_3$ may be combined to form an alkylene having up to four carbon atoms. The term "alkyl" is understood to include primary, secondary and tertiary alkyl radicals.

Representative compounds of the present invention include those in which the R—$R_3$ groups of the above formula include methyl, ethyl, propyl, isopropyl, n-butyl, primary isobutyl, secondary isobutyl, tertiary butyl, n-amyl, branch chain amyls, the normal and branched hexyls, heptyls, octyls, nonyls, and decyls.

The preferred compounds used as active ingredients in the herbicidal compositions of the present invention are those in which X is chlorine, bromine or iodine and, in particular chlorine, and R—$R_3$ are $C_{1-5}$ alkyls.

The specific compound of preference is 2'-methyl-6'-(2,2-dimethoxyethyl)-N-(methoxymethyl)-2-chloroacetanilide.

The herbicidal compositions herein are useful as selective herbicides by applying them to the locus of undesirable plants to be controlled and desirable plants to be protected.

The novel process described herein involves the reaction of the appropriate primary amine of the formula

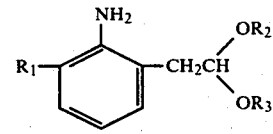

wherein the Rs are $C_{1-10}$ alkyl groups which may be the same or different with formaldehyde to form the corresponding azomethine compound which is reacted with a haloacetylating agent such as chloroacetyl chloride to form the corresponding N-halomethyl-2-haloacetanilide adduct which is then reacted with the appropriate alcohol to form the final product defined above. In general, the reaction between the primary amine and formaldehyde are conducted at temperatures within the range of from about 25° C. to 180° C., and the haloacetylation and alcoholysis steps are conducted at temperatures within the range of −80° C. to 100° C., although higher or lower temperatures may be used.

The process conditions are not critical although best conducted at temperatures within the above ranges for sufficient reaction times and pressures (which may be subatmospheric or superatmosphere) as to assure complete reaction. In like manner, concentrations of reactants are not critical, but will be understood by those skilled in the art that ratios of reactants will be appropriately selected by those skilled in the art following the detailed description and working embodiments herein.

The invention will be more clearly understood by reference to the following detailed description. In the examples, all temperatures are in degrees Centigrade.

DETAILED DESCRIPTION OF THE INVENTION

EXAMPLE 1

This example describes the preparation of 2'-methyl-6'-(2,2-dimethoxyethyl)-N-(methoxymethyl)-2-chloroacetanilide.

6-(2,2-dimethoxyethyl)-2-methylphenylazomethine (2.0 g, 0.01 mol) was placed in 50 ml $CCl_4$, cooled by means of an ice/acetone bath and 1.5 g chloroacetyl chloride (CAC) in $CCl_4$ added. Nmr of this solution indicated that reaction had taken place with formation of CAC adduct. While still cold, 0.012 mol sodium methoxide in 2.6 g of 25% solution of $CH_3OH$ was added, keeping temperature low. The mixture was allowed to warm to room temperature, washed once with water, then vacuum treated to remove volatiles. The amber oil residue remaining was identified by Nmr and elemental analysis as compound mentioned in the first sentence of this example.

Analysis Calc'd for $C_{15}H_{22}ClNO_4$ (percent): C, 57.05; H, 7.02; N, 4.44. Found: C, 58.5; H, 7.02; N, 4.97.

The above azomethine starting material was prepared as follows:

To a one liter four-necked flask fitted with a dropping funnel whose pliable extension fitted nearly to the bottom of the reacting vessel was added 0.22 mol redistilled (middle-cut) o-toluidine (23.8 g) and 600 ml $CH_2Cl_2$. The dropping funnel was surrounded by a cooling jacket. The mixture under nitrogen was cooled to −72° C. by exterior dry ice-acetone cooling. To this solution was added dropwise 23.3 g t-butylhypochlorite contained in 50 ml $CH_2Cl_2$. The solution turned brown at this stage. After stirring ½ hour after the ten minute addition, 0.11 mol of 2,2-dimethoxyethyl methyl sulfide was added, contained in 50 ml $CH_2Cl_2$. Temperature was not permitted to rise above −65° C. The solution turned black/red with some traces of crystals. Mixture permitted to stir for 1.5 to 2.5 hours, then excess triethyl amine was added (15 g), and the mixture allowed to warm to room temperature. At this stage it was permissible to allow the reaction to stand overnight. Water (ca 100 ml) was added, and the mixture stirred, then the layers separated. After vacuum removal of solvent the residue was distilled in several fractions, monitoring purity of desired product by GLC. The product identified by Nmr and elemental analysis as 2-methyl-6-(2,2-dimethoxy-1-methylthioethyl) aniline had a boiling point of 135°–151° C. at 0.2 mm Hg and was obtained in 27% yield.

| Analysis for $C_{12}H_{19}NO_2S$: | | |
|---|---|---|
| | Calc'd | Found |
| C | 59.72 | 59.69 |
| N | 5.80 | 5.84 |
| S | 13.29 | 13.32 |

Sixteen grams (0.067 mol) of above aniline was mixed with 130 g fresh W-2 Raney Ni in 300 ml ethanol. The Raney nickel had previously been triturated with 3×200 ml volumes of ethanol. The reducing agent was stirred with substrate for at least one hour, then the contents decanted from the Raney nickel, which had been allowed to settle, and filtered through a fluted filter. The Raney nickel was twice successively washed with 200 ml portions of ethanol and the extracts filtered through the fluted filter and combined with the original filtrate. The ethanol solution was then evaporated under vacuum, and the gel-like residue treated with water, at the same time adding ether. The ether extract was dried over $MgSO_4$, evaporated and the residue distilled to give bp 96°–100° C. (0.03–0.05 mm). GLC showed 79% assay. However, the 6-(2,2-dimethoxyethyl)-o-toluidine solidified, and was recrystallized from hexane, mp 44°–46° C. Nmr ($CCl_4$) & 2.1 (s, 3, $ArCH_3$), 2.7 (d, 2, J=5 Hz, $ArCH_2CH$), 3.25 (s, 6, $(OCH_3)_2$, 3.8 (broad s, 2, $NH_2$), 4.4 [t, 1, J=5 Hz $CH_2CH$ $(OCH_3)_2$], 6.3–7.0 (multiplet, 3, ArH).

6-(2,2-Dimethoxyethyl)-o-toluidine (6.2 g) was mixed with 1.5 g of freshly pulverized paraformaldehyde and ca 0.3 ml triethyl amine. The material was heated at 150 mm pressure to 90° C. for ca ¾ hour. After this time the vacuum was increased to remove all water, excess formaldehyde, and amine. The azomethine product, 6-(2,2-dimethoxyethyl)-2-methylphenylazomethine, was then distilled at 110° C. (0.15 mm). Assay by GLC showed 90% assay, with total yield 3.8 g. Nmr ($CCl_4$) & 2.0 (s, 3, $ArCH_3$), 2.6 (d, 2, J=5 Hz, $ArCH_2CH$), 3.15 (s, 6, $(OCH_3)_2$), 4.4 (t, 1, J=5 Hz, $ArCH_2CH$), 6.7–7.0 (multiplet, 3, ArH), 7.45 (AB quartet, 2, J=20 Hz, $N=CH_2$).

EXAMPLES 2 TO 46

The compounds in the following examples may also be prepared by substantial repetition of the general procedure set forth in the foregoing example, modified as to reaction temperatures, times, solvents, etc., to account for the nature of the particular reactants, as will be apparent to those skilled in the art. In the examples, the individual compounds are those whose members are identified by the general formula $$XCH_2\overset{\overset{O}{\|}}{C}-N-CH_2OR$$

with $R_1$ on the benzene ring and $CH_2-C\underset{OR_3}{\overset{OR_2}{\diagup}}H$

| Example | R | $R_1$ | $R_2$ | $R_3$ | X |
|---|---|---|---|---|---|
| 2 | methyl | ethyl | methyl | methyl | Cl |

-continued

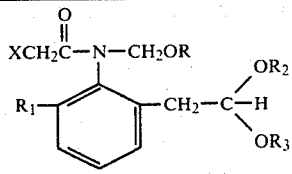

| Example | R | R₁ | R₂ | R₃ | X |
|---|---|---|---|---|---|
| 3 | methyl | n-propyl | methyl | methyl | Cl |
| 4 | methyl | n-butyl | methyl | methyl | Cl |
| 5 | methyl | t-butyl | methyl | methyl | Cl |
| 6 | methyl | amyl | methyl | methyl | Cl |
| 7 | methyl | hexyl | methyl | methyl | Cl |
| 8 | methyl | heptyl | methyl | methyl | Cl |
| 9 | methyl | octyl | methyl | methyl | Cl |
| 10 | methyl | i-propyl | methyl | methyl | Br |
| 11 | methyl | nonyl | methyl | methyl | Cl |
| 12 | methyl | decyl | methyl | methyl | Cl |
| 13 | ethyl | methyl | ethyl | ethyl | Cl |
| 14 | ethyl | ethyl | ethyl | ethyl | Cl |
| 15 | ethyl | methyl | —CH₂CH₂— | | Cl |
| 16 | ethyl | i-propyl | ethyl | ethyl | Br |
| 17 | ethyl | n-butyl | ethyl | ethyl | Br |
| 18 | ethyl | t-butyl | ethyl | ethyl | Cl |
| 19 | ethyl | amyl | ethyl | ethyl | Cl |
| 20 | ethyl | octyl | ethyl | ethyl | Cl |
| 21 | ethyl | decyl | ethyl | ethyl | Cl |
| 22 | ethyl | ethyl | ethyl | ethyl | Br |
| 23 | n-propyl | methyl | n-propyl | n-propyl | Cl |
| 24 | n-propyl | ethyl | n-propyl | n-propyl | Cl |
| 25 | n-propyl | ethyl | n-propyl | n-propyl | Br |
| 26 | n-propyl | n-propyl | n-propyl | n-propyl | Br |
| 27 | i-propyl | methyl | n-propyl | n-propyl | Cl |
| 28 | i-propyl | ethyl | n-propyl | n-propyl | Cl |
| 29 | i-propyl | propyl | n-propyl | n-propyl | Cl |
| 30 | i-propyl | t-butyl | n-propyl | n-propyl | Cl |
| 31 | t-butyl | methyl | n-butyl | n-butyl | Cl |
| 32 | t-butyl | ethyl | n-butyl | n-butyl | Br |
| 33 | t-butyl | n-propyl | n-butyl | n-butyl | Cl |
| 34 | t-butyl | t-butyl | n-butyl | n-butyl | Cl |
| 35 | t-amyl | methyl | n-amyl | n-amyl | Br |
| 36 | t-amyl | ethyl | n-amyl | n-amyl | I |
| 37 | t-amyl | n-propyl | n-amyl | n-amyl | Cl |
| 38 | t-amyl | i-propyl | n-amyl | n-amyl | Cl |
| 39 | t-amyl | t-butyl | n-amyl | n-amyl | Cl |
| 40 | ethyl | methyl | methyl | methyl | I |
| 41 | ethyl | ethyl | methyl | methyl | I |
| 42 | i-propyl | i-propyl | methyl | methyl | I |
| 43 | t-butyl | methyl | methyl | methyl | I |
| 44 | methyl | methyl | methyl | methyl | Br |
| 45 | methyl | ethyl | ethyl | methyl | Cl |
| 46 | ethyl | i-propyl | methyl | methyl | I |

In order to illustrate the advantage of the present invention, the selective preemergence herbicidal activity of the preferred species of this invention, i.e., the compound of Example 1, representative of 2′-alkyl-6′-(2,2-dialkoxyethyl)-N-alkoxymethyl-2-haloacetanilides, was determined in greenhouse tests on soybeans, sugarbeets, wheat, rice and sorghum and selected weed plants.

The pre-emergent data were obtained as follows:

A good grade of top soil was placed in aluminum pans and compacted to a depth of three-eighths to one-half inch (9.53–12.7 mm) from the top of the pan. On top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth. Approximately 2 weeks after seeding and treating, the plants were observed and the results recorded. The herbicidal rating was obtained by means of a fixed scale based on the percent injury of each plant species. The ratings are defined as follows:

| % Control | Rating |
|---|---|
| 0–24 | 0 - No injury |
| 25–49 | 1 - Slight injury |
| 50–74 | 2 - Moderate injury |
| 75–100 | 3 - Severe injury |

Following the above procedure, the compound of Example 1 was tested at application rates of 5.0 lb/acre (5.6 kilograms/hectare), 1.0 lb/A (1.12 kg/ha) and 0.25 lb/A (0.28 kg/ha) against selected weeds in the above crops. At each rate of application, the soybeans suffered no injury and the sugarbeets exhibited only slight injury. At 0.25 lb/A there was no injury to wheat and only slight to moderate injury at the 1.0 and 5.0 lb/A rates. In similar manner, at the 0.25 and 5.0 lb/A rates rice and sorghum were only slightly to moderately injured, although anomalously rice and sorghum showed severe injury at the 1.0 lb/A rate. In contrast, at 5.0 lb/A and 1.0 lb/A panicum, barnyardgrass and crabgrass suffered severe injury as did downy brome at 1.0 lb/A and barnyardgrass at 0.25 lb/A. Slight injury was also observed in lambsquarters, smartweed and velvet leaf at 5.0 lb/A, in morningglory at 1.0 lb/A. At 0.25 lb/A moderate injury was noted in morningglory, panicum, barnyardgrass and crabgrass.

The selective preemergence data set forth above clearly illustrate the efficacy of the preferred compound representative of the present invention as a selective herbicide useful in the control of undesirable weeds in the presence of such agricultural crops as sugarbeets, soybeans, wheat, sorghum and rice.

In another test of the preemergent activity of the compound of Example 1 it was observed that at 5.0 lb/A, severe injury was exhibited by morningglory, lambsquarters, smartweed, nutsedge, quackgrass, downy brome and barnyardgrass, while johnsongrass was moderately injured and velvet leaf slightly injured.

In a test of its postemergence activity, the compound of Example 1 was found to exhibit moderate injury on morningglory and slight injury on lambsquarters and nutsedge at 10 lb/A (11.2 kg/ha).

The herbicidal compositions of this invention including concentrates which require dilution prior to application contain at least one active ingredient and an adjuvant in liquid or solid form. The compositions are prepared by admixing the active ingredient with an adjuvant including diluents, extenders, carriers and conditioning agents to provide compositions in the form of finely-divided particulate solids, granules, pellets, solutions, dispersions or emulsions. Thus the active ingredient can be used with an adjuvant such as a finely-divided solid, a liquid of organic origin, water, a wetting agent, a dispersing agent, an emulsifying agent or any suitable combination of these.

The compositions of this invention, particularly liquids and wettable powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent" it is understood that wetting agents, dispersing agents, suspending agents and emulsifying agents are included therein. Anionic, cationic and non-ionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, ditertiary acetylenic glycols, polyoxyethylene derivatives of alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin sulfonates, polymeric alkyl, naphthalene sulfonates, sodium naphthalene sulfonate, and polymethylene bisnaphthalenesulfonate.

Wettable powders are water-dispersible compositions containing one or more active ingredients, an inert solid extender and one or more wetting and dispersing agents. The inert solid extenders are usually of mineral origin such as the natural clays, diatomaceous earth and synthetic minerals derived from silica and the like. Examples of such extenders include kaolinites, attapulgite clay and synthetic magnesium silicate. The wettable powders compositions of this invention usually contain from about 0.5 to 95 parts (preferably from 5-20 parts) of active ingredient, from about 0.25 to 25 parts (preferably 1-15 parts) of wetting agent, from about 0.25 to 25 parts (preferably 1.0-15 parts) of dispersant and from 5 to about 95 parts (preferably 5-50 parts) of inert solid extender, all parts being by weight of the total composition. Where required, from about 0.1 to 2.0 parts of the solid inert extender can be replaced by a corrosion inhibitor of anti-foaming agent or both.

Aqueous suspensions may be prepared by mixing together and grinding an aqueous slurry of water-insoluble active ingredient in the presence of dispersing agents to obtain a concentrated slurry of very finely-divided particles. The resulting concentrated aqueous suspension is characterized by its extremely small particle size, so that when diluted and sprayed, coverage is very uniform.

Emulsifiable oils are usually solutions of active ingredient in water-immiscible or partially water-immiscible solvents together with a surface active agent. Suitable solvents for the active ingredient of this invention include hydrocarbons and water-immiscible ethers, esters or ketones.

The aqueous suspensions and emulsifiable oil compositions generally contain from about 5 to 95 parts (preferably 5-50 parts) active ingredient, about 0.25 to 50 parts (preferably 1-25 parts) surface active agent and where required about 4 to 94 parts solvent, all parts being by weight based on the total weight of emulsifiable oil.

Granules are physically stable particulate compositions comprising active ingredient adhering to or distributed through a basic matrix of an inert, finely-divided particulate extender. In order to aid leaching of the active ingredient from the particulate, a surface active agent such as those listed hereinbefore can be present in the composition. Natural clays, pyrophyllites, illite and vermiculite are examples of operable classes of particulate mineral extenders. The preferred extenders are the porous, absorptive, preformed particles such as preformed and screened particulate attapulgite or heat expanded, particulate vermiculite, and the finely-divided clays such as kaolin clays, hydrated attapulgite or bentonitic clays. These extenders are sprayed or blended with the active ingredient to form the herbicidal granules.

The granular compositions of this invention generally contain from about 5 parts to about 30 parts by weight of active ingredient per 100 parts by weight of clay and 0 to about 5 parts by weight of surface active agent per 100 parts by weight of particulate clay. The preferred granular compositions contain from about 10 parts to about 25 parts by weight of active ingredient per 100 parts by weight of clay.

The compositions of this invention can also contain other additaments, for example, fertilizers, other herbicides, other pesticides, safeners and the like used as adjuvants or in combination with any of the above-described adjuvants. Chemicals useful in combination with the active ingredients of this invention include, for example, triazines, ureas, carbamates, acetamides, acetanilides, uracils, acetic acid or phenol derivatives, thiolcarbamates, triazoles, benzoic acids, nitriles and the like such as:

3-amino-2,5-dichlorobenzoic acid
3-amino-1,2,4-triazole
2-methoxy-4-ethylamino-6-isopropylamino-s-triazine
2-chloro-4-ethylamino-6-isopropylamino-s-triazine
2-chloro-N,N-diallylacetamide
2-chloroallyl diethyldithiocarbamate
N'-(4-chlorophenoxy) phenyl-N,N-dimethylurea
1,1'-dimethyl-4,4'-bipyridinium dichloride
isopropyl N-(3-chlorophenyl) carbamate
2,2-dichloropropionic acid
S-2,3-dichloroallyl N,N-diisopropylthiolcarbamate
2-methoxy-3,6-dichlorobenzoic acid
2,6-dichlorobenzonitrile
N,N-dimethyl-2,2-diphenylacetamide
6,7-dihydrodipyrido(1,2-a:2',1'-c)-pyrazidiinium salt
3-(3,4-dichlorophenyl)-1,1-dimethylurea
4,6-dinitro-o-sec-butylphenol
2-methyl-4,6-dinitrophenol
ethyl N,N-dipropylthiolcarbamate
2,3,6-trichlorophenylacetic acid
5-bromo-3-isopropyl-6-methyluracil
3-(3,4-dichlorophenyl)-1-methoxy-1-methylurea
2-methyl-4-chlorophenoxyacetic acid
3-(p-chlorophenyl)-1,1-dimethylurea
1-butyl-3-(3,4-dichlorophenyl)-1-methylurea
N-1-naphthylphthalamic acid
1,1'-dimethyl-4,4'-bipyridinium salt
2-chloro-4,6-bis(isopropylamino)-s-triazine
2-chloro-4,6-bis(ethylamino)-s-triazine
2,4-dichlorophenyl-4-nitrophenyl ether
alpha, alpha, alpha-trifluoro-2,6-dinitro-N,N-dipropyl-p-toluidine
S-propyl dipropylthiolcarbamate
2,4-dichlorophenoxyacetic acid
N-isopropyl-2-chloroacetanilide
2',6'-diethyl-N-methoxymethyl-2-chloroacetanilide
2'-methyl-6'-ethyl-N-(2-methoxyprop-2-yl)-2-chloroacetanilide
monosodium acid methanearsonate
disodium methanearsonate
N-(1,1-dimethylpropynyl)-3,5-dichlorobenzamide
N-(phosphonomethyl) glycine and its $C_{1-6}$ monoalkyl amine and alkali metal salts and combinations thereof in ratios of 1-4 lb/acre (1.12-4.48 kg/ha) to 1-10 lb/acre of compounds of this invention.

Fertilizers useful in combination with the active ingredients include for example ammonium nitrate, urea, potash, and superphosphate. Other useful additaments include materials in which plant organisms take root and grow such as compost manure, humus, sand and the like.

When operating in accordance with the present invention, effective amounts of the acetanilides of this invention are applied to the soil containing the plants, or are incorporated into aquatic media in any convenient fashion. The application of liquid and particulate solid compositions to the soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds of this invention to the locus of undesired weeds is essential and critical for the practice of the present invention. The exact amount of active ingredient to be employed is dependent upon various factors, including the plant species and stage of development thereof, the type and condition of soil, the amount of rainfall and the specific acetanilide employed. In selective preemergence application to the plants or to the soil a dosage of from 0.02 to about 11.2 kg/ha, preferably from about 0.04 to about 5.60 kg/ha, or suitably from 1.12 to 5.6 kg/ha of acetanilide is usually employed. Lower or higher rates may be required in some instances. One skilled in the art can readily determine from this specification, including the above example, the optimum rate to be applied in any particular case.

The term "soil" is employed in its broadest sense to be inclusive of all conventional "soils" as defined in Webster's New International Dictionary, Second Edition, Unabridged (1961). Thus the term refers to any substance of media in which vegetation may take root and grow, and includes not only earth but also compost, manure, muck, humus, sand and the like, adapted to support plant growth.

Although the invention is described with respect to specific modifications, the details thereof are not to be construed as limitations except to the extent indicated in the following claims.

I claim:

1. Compounds having the formula

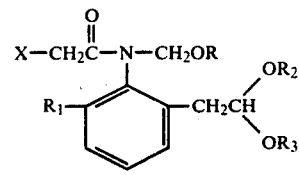

wherein X represents chloro, bromo or iodo and R, $R_1$, $R_2$ and $R_3$ represent $C_{1-10}$ alkyl radicals which may be the same or different.

2. Compounds according to claim 1 wherein X is chlorine.

3. Compound according to claim 2 which is 2'-methyl-6'-(2,2-dimethoxyethyl)-N-(methoxymethyl)-2-chloroacetanilide.

4. Herbicidal compositions comprising an inert adjuvant and an effective amount of a compound having the formula

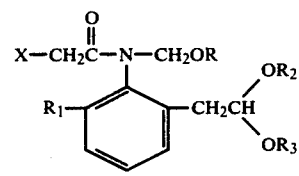

wherein X represents chloro, bromo or iodo and R, $R_1$, $R_2$ and $R_3$ represent $C_{1-10}$ alkyl radicals which may be the same or different.

5. Compositions according to claim 4 wherein in said compound X is chlorine.

6. Compositions according to claim 5 wherein said compound is 2-methyl-6'-(2,2-dimethoxyethyl)-N-(methoxymethyl)-2-chloroacetanilide.

7. A method for controlling undesirable vegetation which comprises applying to the locus thereof a herbicidal composition comprising an inert adjuvant and an effective amount of a compound having the formula

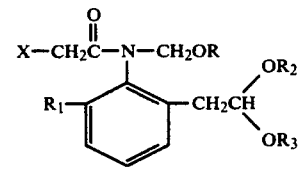

wherein X represents chloro, bromo or iodo and R, $R_1$, $R_2$ and $R_3$ represent $C_{1-10}$ alkyl radicals which may be the same or different.

8. Method according to claim 7 wherein in said compound X is chlorine.

9. Method according to claim 8 wherein said compound is 2-methyl-6'-(2,2-dimethoxyethyl)-N-(methoxymethyl)-2-chloroacetanilide.

* * * * *